(12) United States Patent
Jacky et al.

(10) Patent No.: US 10,912,823 B2
(45) Date of Patent: Feb. 9, 2021

(54) BOTULINUM NEUROTOXIN FOR TREATMENT OF DISORDERS ASSOCIATED WITH MELANOCYTE HYPERACTIVITY AND/OR EXCESS MELANIN

(71) Applicant: Allergan, Inc., Irvine, CA (US)

(72) Inventors: Birgitte P.S. Jacky, Orange, CA (US); Shiazah Z. Malik, Irvine, CA (US); Joanne Wang, Irvine, CA (US); Yi Liu, Irvine, CA (US); Amy Brideau-Andersen, San Clemente, CA (US); Lance E. Steward, Irvine, CA (US); Linh Q. Le, Tustin, CA (US); Edward C. Hsai, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/992,627

(22) Filed: May 30, 2018

(65) Prior Publication Data

US 2018/0344820 A1 Dec. 6, 2018

Related U.S. Application Data

(60) Provisional application No. 62/512,792, filed on May 31, 2017.

(51) Int. Cl.
| | | |
|---|---|---|
| *A61K 38/48* | (2006.01) | |
| *A61P 17/00* | (2006.01) | |
| *A61K 9/00* | (2006.01) | |
| *A61K 8/99* | (2017.01) | |
| *A61Q 19/02* | (2006.01) | |

(52) U.S. Cl.
CPC ............ *A61K 38/4893* (2013.01); *A61K 8/99* (2013.01); *A61K 9/0014* (2013.01); *A61K 9/0021* (2013.01); *A61P 17/00* (2018.01); *A61Q 19/02* (2013.01); *A61K 2800/91* (2013.01)

(58) Field of Classification Search
None
See application file for complete search history.

(56) References Cited

U.S. PATENT DOCUMENTS

| | | | | |
|---|---|---|---|---|
| 9,504,735 | B2* | 11/2016 | Sanders | A61K 38/4886 |
| 9,744,237 | B2* | 8/2017 | Moazed | A61K 9/0048 |
| 10,113,159 | B2* | 10/2018 | Madec | A61K 38/4893 |
| 10,245,305 | B2* | 4/2019 | First | A61K 38/4893 |
| 2005/0220734 | A1* | 10/2005 | First | A61K 8/64 424/62 |
| 2012/0195878 | A1* | 8/2012 | Haag-Molkenteller | A61K 38/4893 424/94.67 |
| 2014/0276359 | A1* | 9/2014 | Alvarez | A61K 33/00 604/21 |
| 2015/0216953 | A1* | 8/2015 | First | A61K 38/4893 424/62 |
| 2017/0304601 | A1* | 10/2017 | Gardner | A61N 1/327 |
| 2018/0344820 | A1* | 12/2018 | Jacky | A61P 17/00 |
| 2019/0185523 | A1* | 6/2019 | Jacky | A61Q 19/08 |

FOREIGN PATENT DOCUMENTS

| | | | | |
|---|---|---|---|---|
| WO | WO-2012103415 A1 * | 8/2012 | ......... | A61K 38/4893 |
| WO | WO-2016048689 A1 * | 3/2016 | ............ | A61N 1/327 |
| WO | WO-2018093465 A1 * | 5/2018 | ............ | A61Q 19/08 |
| WO | WO-2018222652 A1 * | 12/2018 | ............... | A61K 8/99 |

OTHER PUBLICATIONS

Basar et al, Turk J Ophthalmol, 2016, 46:282-290 (Year: 2016).*
Lanoue et al, Cutis, Sep. 2016, 98:163-167 (Year: 2016).*
Schlessinger et al, Aesthetic Surgery Journal, Jul. 2011, 31/5:529-539 (Abstract Only) (Year: 2011).*
Walker et al, J Clin Aesthet Dermatol., Feb. 2014, 7/2:31-39. (Year: 2014).*
Moura et al, FEMS Immunology and Medical Microbiol., Apr. 1, 2011, 61:288-300. published online: Jan. 26, 2011 (Year: 2011).*
Hyperkeratosis What Is It?, Everyday Health. Com, May 19, 2010, 2 Pages, US Pamphlet.
American College of Foot and Ankle Surgeons, Hammertoe, American College of Foot and Ankle Surgeons, 2004, 2 Pages, US Pamphlet.
Amy E. Rose, et al., Safety and Efficacy of Intradermal Injection of Botulinum Toxin for the Treatment of Oily Skin, American Society for Dermatologic Surgery, Inc., 2013, pp. 443-448, vol. 39.
Arthur K. Balin, Seborrheic Keratosis, emedicine, Jan. 6, 2009, 26 pages.
Cedric Woudstra, et al., Neurotoxin Gene Profiling of Clostridium Botulinum Types C and D Native to Different Countries in Europe, Applied and Environmental Microbiology, 2012, pp. 3120-3127, vol. 78, No. 9.
Daniel J. Stulberg, et al., Common Hyperpigmentation Disorders in Adults: Part II. Melanomama, Seborrheic Keratoses, Acanthosis Nigricans, Melasma, Diabetic Dermopathy, Tinea Versicolor, and Postinflammatory Hyperpigmentation, American Family Physician, Nov. 13, 2003, 1963-1968, 68 (10), US.

(Continued)

*Primary Examiner* — Nita M. Minnifield
(74) *Attorney, Agent, or Firm* — Brigitte C. Phan

(57) ABSTRACT

Methods for treating melanin-related afflictions of the skin, such as hyperpigmentation, are provided. The methods comprise administering a composition comprising BoNT/DC.

20 Claims, 3 Drawing Sheets

(56) References Cited

OTHER PUBLICATIONS

Daniel L. Stulberg, et al., Common Hyperpigmentation Disorders in Adults: Part I. Diagnostic Approach, Cafe au Lait Macules, Diffuse Hyperpigmentation, Sun Exposure, and Phototoxic Reactions, American Family Physician, Nov. 15, 2003, 1955-1960, 68 (10), US.

Glynis Scott and Qian Zhao, Rab3a and SNARE Proteins: Potential Regulators of Melanosome Movement, The Society for Investigative Dermatology, Inc., 2001, pp. 296-304, vol. 116, No. 2.

Guorui Yao, et al., Crystal Structure of the Receptor-Binding Domain of Botulinum Neurotoxin Type HA, Also known as Type FA or H, Toxins, 2017, pp. 1-13, 9, 93.

Hanna Skarin, et al., Plasmidome Interchange between Clostridium botulinum, Clostridium novyi and Clostridium haemolyticum Converts Strains of independent Lneages ito Distinctly Different Pathogens, PLOS ONE, 2014, pp. 1-14, vol. 9, Issue 9.

Hercules Moura, et al., Studies on Botulinum Neurotoxins Type /C1 and mosaic/DC using Endopep-MS and proteomics, FEMS Immunology & Medical Microbiology, 2011, pp. 288-300, vol. 61.

Irene Zornetta, et al., The first non clostridial botulinum like toxin cleaves VAMP within the juxtamembrane domain, Scientific Reports, 2016, pp. 1-10, 6:30257.

Karolien Van De Bossche et al., The Quest for the Mechanism of Melanin Transfer, Traffic, 2006, pp. 768-778, 7:, Department of Dermatologym Ghent Unv. Hospital, Belguim.

Keiji Nakamura, et al., Characterization of the D/C mosaic neurotoxin produced by clostridium botulinum associated with bovine botulism in Japan, Veterinary Microbiology, 2010, 147-154, vol. 140.

Keiji Nakamura, et al., Unique Biological Activity of Botulinum D/C Mosaic Neurotoxin in Murine Species, Infection and Immunity, 2012, pp. 2886-2893, vol. 80, No. 8.

Kohji Moriishi, et al., Molecular Diversity of Neurotoxins form Clostridium botulinum type D Strains, Infection and Immunity, 1989, pp. 2886-2891, vol. 57, No. 9.

Kohji Moriishi, et al., Mosaic Structures of Neurotoxins produced from Clostridium botulinum Types C and D Organisms, BBA Biochimica et Biophysica Acta, 1996, pp. 123-126, 1307.

Lisheng Peng, et al., Botulinum neurotoxin D-C uses synaptotagmin I and II as receptors, and human synaptotagmin II is not an effective receptor for type B, D-C and G toxins, Journal of Cell Science, 2012, 3233-3242, 125(13).

Ornella Rossetto, et al., Botulinum neurotoxins: genetic, structural and mechanistic insights, Nature Reviews Microbiology, 2014, pp. 535-549, vol. 12.

Robert P. Webb et al., Protection with Recombinant Clostridium Botulinum C1 nd D Bindng Domain Subunit (Hc) Vaccines Against C and D Neurotoxins, Vaccine, 2007, pp. 4273-4282, Vaccine 25, Science Direct.

Sam Gibbs, et al., Local Treatments for Cutaneous Warts, BMJ Journals, Aug. 2002, 8 Pages, 325.

Sicai Zhang, et al., Structural Basis for the Unique Ganglioside and Cell Membrane Recognition Mechanism of Botulinum Neurotoxin DC, Nature Cmmunications, 2017, pp. 1-12, 8:1637.

Swartling, S., et al., Treatment of Dyshidratic Hand Dermatitis With Intradermal Botulinum Toxin, 151, 2.

T.J. Smith, et al., Sequence Variation within Botulinum Neurotoxin Serotypes Impacts Antibody Binding and Neutralization, Infection and Immunity, 2005, pp. 5450-5457, vol. 73, No. 9.

* cited by examiner

BOTULINUM NEUROTOXIN FOR TREATMENT OF DISORDERS ASSOCIATED WITH MELANOCYTE HYPERACTIVITY AND/OR EXCESS MELANIN

CROSS-REFERENCE TO RELATED APPLICATIONS

This application claims the benefit of U.S. Provisional Application No. 62/512,792, filed May 31, 2017, which is hereby incorporated by reference in its entirety.

TECHNICAL FIELD

The subject matter described herein relates to methods for treating melanin-related afflictions of the skin, in particular hyper melanin related afflictions such as hyperpigmentation, by administering a composition comprising a clostridial toxin, such as a botulinum neurotoxin, and in particular the botulinum neurotoxin BoNT/DC mosaic.

BACKGROUND

Melanocytes are specialized cells present in the skin which make and distribute the pigment melanin to surrounding keratinocytes, another type of skin cell. The color of the skin, hair and iris of the eyes is determined primarily by the presence or absence of melanin. Melanocyte metabolism, including melanin production, (i.e. hair color and skin color) is regulated at least in part by various substances released primarily by keratinocytes in response to hormones and UV exposure.

Skin and hair pigment disorders, also referred to as melanin related afflictions, include melasma, pigment loss after skin damage, vitiligo, freckles, moles including lipomas moles (nevi) and atypical moles (dysplastic nevi), dermatofibromas, dermoid cyst, keloids, keratoacanthomas, pyogenic granulomas, seborrheic keratoses, actinic keratosis, skin tags, melanoma and solar lentigo.

Certain proteins, such as the SNAP (Soluble NSF Attachment Protein) Receptor (SNARE) proteins, including Syntaxin-3 (Stx-3), Synaptosomal-associated protein 23 (SNAP-23), and vesicle-associated membrane protein (VAMP, also called synaptobrevin) may impact melanin content in melanocytes (Yatsu et al., *J Invest Dermatol*, 133(9), 2237-2246, 2013). Cleavage, binding, and/or sequestering of vesicle-associated membrane proteins, such as VAMP-2, may disrupt melanocyte intracellular vesicular trafficking and block melanogenesis (pigment formation) in melanosomes (specialized pigment containing vesicles) and/or release or transfer of vesicles, for example melanosomes containing melanin. VAMP-2 is expressed in melanocytes and perhaps associated with melanosomes and SNAP-23 (Scott and Zhao, *J Invest Dermatol*, 116(2), 296-304, 2001; Van Den Bossche et al., *Traffic*, 7(7), 769-778 2006; Wade et al., *J. Biol. Chem.*, 276(23), 19820-19827, 2001).

Hyperpigmentation, an aberrant uneven skin color with patches of darkened spots, is associated with several skin disorders, including melasma and solar lentigo, commonly known as "age spots" or "liver spots". Treatments for hyperpigmentation include (1) prescription topical bleaching agents, such as 4% hydroquinone (HQ), Tri-Luma (combination of hydroquinone, tretinoin and fluocinolone), retinoids (e.g. treninoid, adapalene and tazarotene); (2) medical procedures to remove or destroy pigment, such as chemical exfoliation and laser therapy; and (3) over the counter drugs and cosmetics, such as 20 HQ and various herbal extracts. Current hyperpigmentation treatments have several side effects including skin irritation and inflammation, which is a driver for additional hyperpigmentation as it can lead to post-inflammatory hyperpigmentation.

Agents and methods for treating melanin related afflictions and more particularly hyper-melanin related afflictions are needed. The present compositions and methods are directed to meeting this need.

BRIEF SUMMARY

In one aspect, the present disclosure provides methods of treating a melanin related affliction, the methods comprise providing or administering a botulinum neurotoxin (BoNT) mosaic, such as BoNT/DC mosaic.

In one embodiment, the melanin related affliction is a disorder or disease associated with melanocyte hyperactivity and/or excess melanin. In one embodiment, the melanocyte hyperactivity results in hyperpigmentation and/or aberrant pigmentation. In other embodiments, the affliction is, for example, melasma, solar lentigo (solar lentigines), nevi, or melanoma.

In some embodiments, a liquid or solid pharmaceutical composition comprising the botulinum neurotoxin mosaic is provided. In one embodiment, the botulinum neurotoxin mosaic is BoNT/DC mosaic.

In one embodiment, the pharmaceutical composition is a liquid composition and is administered via injection. In embodiments, the injection is intramuscular, intracutaneous, intradermally or subcutaneous. In another embodiment, the pharmaceutical composition is a liquid composition or a solid composition, and is administered transdermally or topically.

In one aspect, a method of cleaving VAMP-2 is provided, the method comprises providing or administering a botulinum neurotoxin (BoNT). In some embodiments, the botulinum neurotoxin is a BoNT mosaic. In one embodiment, the BoNT is BoNT/DC mosaic.

BRIEF DESCRIPTION OF DRAWINGS

FIG. 1A shows a western blot of glyceraldehyde 3-phosphate dehydrogenase (GAPDH; upper band, loading control) and vesicle-associated membrane protein (VAMP-2, lower band) in mouse melanocyte cells after treatment with buffer (untreated or negative control), BoNT/A, BoNT/B, BoNT/D, BoNT/DC, or a variant of BoNT/D lacking the binding domain portion, LHn/D;

FIG. 1B is a graph showing the amount of VAMP-2, normalized to the amount of GAPDH, and shown as percent of the untreated control, based on the western blot band intensities shown in FIG. 1A, in mouse melanocyte cells after treatment with buffer (untreated or negative control, BoNT/A, BoNT/B, BoNT/D, BoNT/DC, or a variant of BoNT/D lacking the binding domain portion, LHn/D;

DETAILED DESCRIPTION

I. Definitions

Figure 2A:
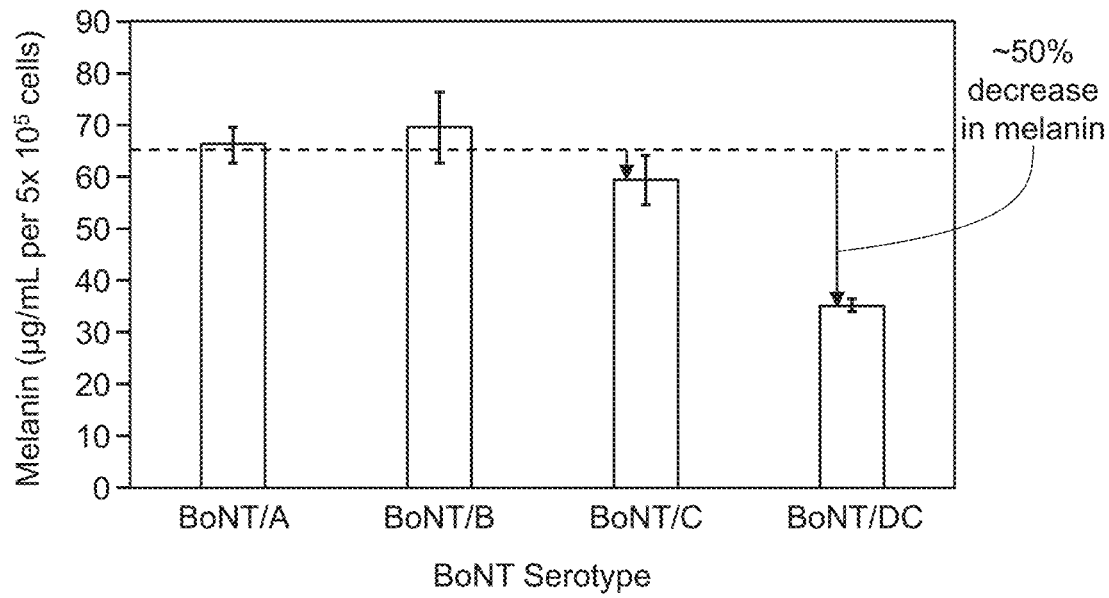
FIG. 2A is a bar graph showing melanin level in mouse melanocyte cells, in μg/mL per $5 \times 10^5$ cells, after treatment with BoNT/A, BoNT/B, BoNT/C, or BoNT/DC.

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value.

"Administration", or "to administer" means the step of giving (i.e. administering) a pharmaceutical composition to a subject, or alternatively a subject receiving a pharmaceutical composition. The pharmaceutical compositions disclosed herein can be locally administered by various methods. For example, intramuscular, intradermal, subcutaneous administration, intrathecal administration, intraperitoneal administration, topical (transdermal), instillation, and implantation (for example, of a slow-release device such as polymeric implant or miniosmotic pump) can all be appropriate routes of administration.

"Alleviating" means a reduction in the occurrence of a symptom or of a condition or disorder. Thus, alleviating includes some reduction, significant reduction, near total reduction, and total reduction.

"Botulinum toxin" and "Botulinum neurotoxin" (BoNT) are used interchangeably. They mean a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F, G and X (Stenmark, unpublished data), and their subtypes and any other types of subtypes thereof, and mosaic, including DC, CD (Moriishi et al. 1996, Webb et al., 2007, Nakamura et al. 2010, Peng et al. 2012, Rossetto et al. 2014, Berntsson et al. 2013) and FA (Also known as H, Yao et al. 2017) or any re-engineered proteins, analogs, derivatives, homologs, parts, sub-parts, variants, or versions, in each case, of any of the foregoing. "Botulinum toxin" as used herein, also encompasses a "modified botulinum toxin". Further "botulinum toxin" as used herein also encompasses a botulinum toxin complex (for example, the 300, 550 (BoNT/DC, Moura et al. 2011), 600 and 900 kDa complexes, as well as the neurotoxic component of the botulinum toxin (150 kDa) that is unassociated with the complex proteins. Botulinum toxin serotypes A, B, C, D, E, F, G and mosaic such as DC may be noted as BoNT/A, BoNT/B, BoNT/C, BoNT/D, BoNT/E, BoNT/F, BoNT/G, and BoNT/DC, respectively.

"Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate. Non-limiting examples of Clostridial toxins include a Botulinum toxin like BoNT/A, a BoNT/B, a BoNT/$C_1$, a BoNT/D, a BoNT/E, a BoNT/F, a BoNT/G, a BoNT/DC mosaic, a Tetanus toxin (TeNT), a *Baratii* toxin (BaNT), and a *Butyricum* toxin (BuNT). The BoNT/$C_2$ cytotoxin and BoNT/$C_3$ cytotoxin, not being neurotoxins, are excluded from the term "Clostridial toxin." A Clostridial toxin disclosed herein includes, without limitation, naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, Clostridial toxin chimeric variants and active Clostridial toxin fragments thereof, or any combination thereof. A Clostridial toxin disclosed herein also includes a Clostridial toxin complex as well as the neurotoxic component of the clostridial toxin that is unassociated with the complex proteins. As used herein, the term "Clostridial toxin complex" refers to a complex comprising a Clostridial toxin and non-toxin associated proteins (NAPs), such as, e.g., a Botulinum toxin complex, a Tetanus toxin complex, a *Baratii* toxin complex, and a *Butyricum* toxin complex. Non-limiting examples of Clostridial toxin complexes include those produced by a *Clostridium botulinum*, such as, e.g., a 900 kDa BoNT/A complex, a 500 kDa BoNT/A complex, a 300 kDa BoNT/A complex, a 500 kDa BoNT/B complex, a 500 kDa BoNT/$C_1$ complex, a 500 kDa BoNT/D complex, a 300 kDa BoNT/D complex, a 300 kDa BoNT/E complex, a 300 kDa BoNT/F complex, a 550 kDa BoNT/DC complex, and a 300 kDa BoNT/DC complex.

"Clostridial toxin active ingredient" refers to a molecule which contains any part of a clostridial toxin that exerts an effect upon or after administration to a subject or patient. As used herein, the term "clostridial toxin active ingredient" encompasses a Clostridial toxin complex comprising the approximately 150-kDa Clostridial toxin and other proteins collectively called non-toxin associated proteins (NAPs), the approximately 150-kDa Clostridial toxin alone, or a modified Clostridial toxin, such as, e.g., a re-targeted Clostridial toxins.

"Effective amount" as applied to the biologically active ingredient means that amount of the ingredient which is generally sufficient to effect a desired change in the subject. For example, where the desired effect is a reduction in a symptom associated with a melanin related disorder, an effective amount of the ingredient is that amount which causes at least a substantial reduction of the symptom, and without resulting in significant toxicity.

"Effective amount" when used in reference to the amount of an excipient or specific combination of excipients added to a Clostridial toxin composition, refers to the amount of each excipient that is necessary to achieve a composition of a Clostridial toxin active ingredient having a desired stability and/or activity. In other aspects of this embodiment, a therapeutically effective concentration of a Clostridial toxin active ingredient reduces a symptom associated with an aliment, such as for example a melanin related afflictions, by, e.g., at most 10%, at most 20%, at most 30%, at most 40%, at most 50%, at most 60%, at most 70%, at most 80%, at most 90% or at most 100%.

"Heavy chain" or "HC" means the heavy chain of a botulinum neurotoxin. It has a molecular weight of about 100 kDa and can also be referred to as the H chain.

$H_C$ means a fragment (about 50 kDa) derived from the heavy chain of a botulinum neurotoxin which is approximately equivalent to the carboxyl end segment of the heavy chain, or the portion corresponding to that fragment in the intact heavy chain. It is believed to contain the portion of the natural or wild type botulinum neurotoxin involved in high affinity, presynaptic binding to a target cell, such as for example melanocytes.

$H_N$ means a fragment (about 50 kDa) derived from the heavy chain of a botulinum neurotoxin which is approximately equivalent to the amino end segment of the heavy chain, or the portion corresponding to that fragment in the intact in the heavy chain. It is believed to contain the portion of the natural or wild type botulinum neurotoxin involved in the translocation of the light chain across an intracellular endosomal membrane.

"Light chain" or "LC" means the light chain of a clostridial neurotoxin. It has a molecular weight of about 50 kDa, and can be referred to as the L chain, L, or as the proteolytic domain (amino acid sequence) of a botulinum neurotoxin.

LC-HN/LHN means fragment of BoNT (about 100 kDa) comprised of the light chain and translocation domain. Similarly, LC-HN of BoNT/A, BoNT/B, BoNT/C, BoNT/D, BoNT/E, BoNT/F, BoNT/G, mosaic DC may be referred to as LC-HN/A, LC-HN/B, LC-HN/C, LC-HN/D, LC-HN/E, LC-HN/F, LC-HN/G, and LC-HN/DC, respectively.

$LH_N$ or $L-H_N$ means a fragment derived from a clostridial neurotoxin that contains the L chain, or a functional fragment thereof coupled to the $H_N$ domain. It can be obtained from the intact clostridial neurotoxin by proteolysis, so as to remove or to modify the $H_C$ domain. Similarly, $LH_N$ of BoNT/A, BoNT/B, BoNT/C, BoNT/D, BoNT/E, BoNT/F, BoNT/G, mosaic DC may be referred to as $LH_N$/A, $LH_N$/B, $LH_N$/C, $LH_N$/D, $LH_N$/E, $LH_N$/F, $LH_N$/G, and $LH_N$/DC, respectively.

"Local administration" means direct administration of a pharmaceutical at or to the vicinity of a site on or within an animal body, at which site a biological effect of the pharmaceutical is desired, such as via, for example, intramuscular or intra- or subdermal injection or topical administration. Local administration excludes systemic routes of administration, such as intravenous or oral administration. Topical administration is a type of local administration in which a pharmaceutical agent is applied to a patient's skin.

"Modified botulinum toxin" means a botulinum toxin that has had at least one of its amino acids deleted, modified, or replaced, as compared to a native botulinum toxin. The modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Mutation" means a structural modification of a naturally occurring protein or nucleic acid sequence. For example, in the case of nucleic acid mutations, a mutation can be a deletion, addition or substitution of one or more nucleotides in the DNA sequence. In the case of a protein sequence mutation, the mutation can be a deletion, addition or substitution of one or more amino acids in a protein sequence. For example, a specific amino acid comprising a protein sequence can be substituted for another amino acid, for example, an amino acid selected from a group which includes the amino acids alanine, asparagine cysteine, aspartic acid, glutamic acid, phenylalanine, glycine, histidine, isoleucine, lysine, leucine, methionine, proline, glutamine, arginine, serine, threonine, valine, tryptophan, tyrosine or any other natural or non-naturally occurring amino acid or chemically modified amino acids. Mutations to a protein sequence can be the result of mutations to DNA sequences that when transcribed, and the resulting mRNA translated, produce the mutated protein sequence. Mutations to a protein sequence can also be created by fusing a peptide sequence containing the desired mutation to a desired protein sequence.

"Patient" means a human or non-human subject receiving medical, cosmetic or veterinary care. Accordingly, the compositions as disclosed herein can be used in treating any animal, such as, for example, mammals, or the like.

"Pharmaceutical composition" means a composition comprising an active pharmaceutical ingredient, such as, for example, a clostridial toxin active ingredient such as a botulinum toxin, and at least one additional ingredient, such as, for example, a stabilizer or excipient or the like. A pharmaceutical composition is therefore a formulation which is suitable for diagnostic, therapeutic or cosmetic administration to a subject, such as a human patient. The pharmaceutical composition can be, for example, in a lyophilized or vacuum dried condition, a solution formed after reconstitution of the lyophilized or vacuum dried pharmaceutical composition, or as a solution or solid which does not require reconstitution.

"Pharmacologically acceptable excipient" is synonymous with "pharmacological excipient" or "excipient" and refers to any excipient that has substantially no long term or permanent detrimental effect when administered to mammal and encompasses compounds such as, e.g., stabilizing agent, a bulking agent, a cryo-protectant, a lyo-protectant, an additive, a vehicle, a carrier, a diluent, or an auxiliary. An excipient generally is mixed with an active ingredient, or permitted to dilute or enclose the active ingredient and can be a solid, semi-solid, or liquid agent. It is also envisioned that a pharmaceutical composition comprising a Clostridial toxin active ingredient can include one or more pharmaceutically acceptable excipients that facilitate processing of an active ingredient into pharmaceutically acceptable compositions. Any pharmacologically acceptable excipient insofar as it is not incompatible with the Clostridial toxin active ingredient, its use in pharmaceutically acceptable compositions is contemplated. Non-limiting examples of pharmacologically acceptable excipients can be found in, e.g., Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

The constituent ingredients of a pharmaceutical composition can be included in a single composition (that is, all the constituent ingredients, except for any required reconstitution fluid, are present at the time of initial compounding of the pharmaceutical composition) or as a two-component system, for example a vacuum-dried composition reconstituted with a reconstitution vehicle which can, for example, contain an ingredient not present in the initial compounding of the pharmaceutical composition. A two-component system can provide several benefits, including that of allowing incorporation of ingredients which are not sufficiently compatible for long-term shelf storage with the first component of the two-component system. For example, the reconstitution vehicle may include a preservative which provides sufficient protection against microbial growth for the use period, for example one-week of refrigerated storage, but is not present during the two-year freezer storage period during which time it might degrade the toxin. Other ingredients, which may not be compatible with a botulinum toxin or other ingredients for long periods of time, can be incorporated in this manner; that is, added in a second vehicle (e.g. in the reconstitution vehicle) at the approximate time of use. A pharmaceutical composition can also include preservative agents such as benzyl alcohol, benzoic acid, phenol, parabens and sorbic acid. Pharmaceutical compositions can include, for example, excipients, such as surface active agents; dispersing agents; inert diluents; granulating and disintegrating agents; binding agents; lubricating agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; antioxidants; stabilizing agents; and pharmaceutically acceptable polymeric or hydrophobic materials and other ingredients known in the art and described, for example in Genaro, ed., 1985, Remington's Pharmaceutical Sciences, Mack Publishing Co., Easton, Pa., which is incorporated herein by reference.

"Tonicity agent" means a low molecular weight excipient which is included in a formulation to provide isotonicity. Disaccharides, such as trehalose or sucrose, polyalcohols, such as sorbitol or mannitol, monosaccharides, such as glucose, and salt, such as sodium chloride, can serve as a tonicity agent.

"Polysaccharide" means a polymer of more than two saccharide molecule monomers. The monomers can be identical or different.

"Stabilizing agent", "stabilization agent" or "stabilizer" means a substance that acts to stabilize a Clostridial toxin active ingredient such that the potency of the pharmaceutical composition is increased relative to an unstabilized composition.

"Stabilizers" can include excipients, and can include protein and non-protein molecules.

"Therapeutic formulation" means a formulation can be used to treat and thereby alleviate a disorder or a disease, such as, for example, a disorder or a disease associated with a melanin related affliction.

"Topical administration" excludes systemic administration. In other words, and unlike conventional therapeutic transdermal methods, topical administration of botulinum toxin does not result in significant amounts of the neurotoxin passing into the circulatory system of the patient.

"Treating" means to alleviate (or to eliminate) at least one symptom of a condition or disorder, such as, for example, excess melanin, either temporarily or permanently.

"VAMP" means synaptobrevin or vesicle associated membrane protein, which includes VAMP-1, VAMP-2, and VAMP-3.

"Variant" means a clostridial neurotoxin, such as wild-type botulinum toxin serotype A, B, C, D, E, F G, or mosaic DC that has been modified by the replacement, modification, addition or deletion of at least one amino acid relative to wild-type botulinum toxin, which is recognized by a target cell, internalized by the target cell, and catalytically cleaves a SNARE (Soluble NSF Attachment Protein Receptor) protein in the target cell. An example of a variant neurotoxin component can comprise a variant light chain of a botulinum toxin having one or more amino acids substituted, modified, deleted and/or added. This variant light chain may have the same or better ability to prevent exocytosis, for example, the release of neurotransmitter vesicles. Additionally, the biological effect of a variant may be decreased compared to the parent chemical entity. For example, a variant light chain of a botulinum toxin type A having an amino acid sequence removed may have a shorter biological persistence than that of the parent (or native) botulinum toxin type A light chain.

II. Methods of Treatment

Figures 1A, 1B:
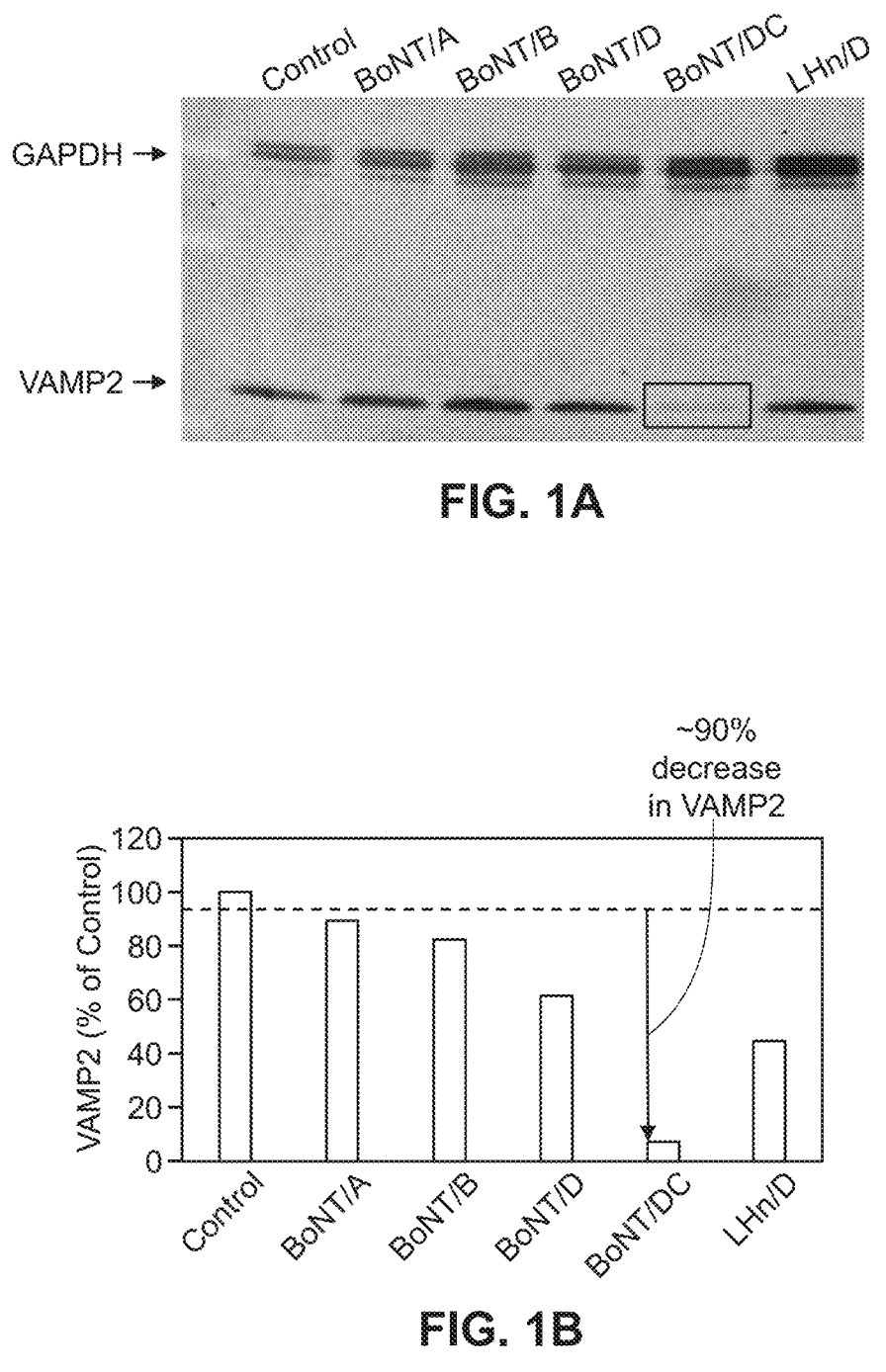

In one aspect, a method for treating a melanin-related affliction in a patient is provided. The method comprises administering to the patient a dose or an amount of a clostridial toxin, such as a botulinum neurotoxin (BoNT) that is effective to reduce melanin content. In some embodiments, the botulinum neurotoxin is a BoNT mosaic, BoNT/DC. In other related aspects, methods for treating a hypermelanin affliction, such as hyperpigmentation, are provided by administering a composition comprising a BoNT. As will be demonstrated herein, in embodiments, the composition comprises a BoNT mosaic, BoNT/DC In a first study, detailed in Example 1, mouse melanocyte cells were treated with the same amount of native BoNT/A, native BoNT/B, recombinant BoNT/D, native BoNT/DC, or recombinant LHn/D—a variant of BoNT/D lacking the binding domain portion. After treatment with the toxins, VAMP-2 and GAPDH were detected by Western Bot, and melanin content was measured. The results are shown in FIGS. 1A-1B.

FIG. 1A shows the Western Blot of GAPDH (upper band, loading control) and VAMP-2 (lower band) protein in the untreated (negative control) or toxin treated mouse melanocyte cells. FIG. 1B is a bar graph showing the amount of VAMP-2, normalized to the amount of GAPDH, and shown as percent of the untreated control (based on Western Blot band intensities shown in FIG. 1A). Treatment of melanocyte cells with BoNT/DC, but not BoNT/A, BoNT/B, BoNT/D or LHn/D, resulted in >90% decrease in VAMP-2. Accordingly, in one aspect, a method for cleaving VAMP-2 in melanocytes cells of the skin by administering to a subject an amount of BoNT/DC is contemplated. The reduction of intact VAMP-2 in the melanocytes of the skin results in a decrease in melanin content. In another aspect, a method of decreasing melanin content in melanocyte cells of the skin is contemplated, by administering to a subject an amount of BoNT/DC to decrease VAMP-2 levels in the skin or in the cells, and thereby decrease melanin content in the skin and/or melanocytes.

Figure 2B:
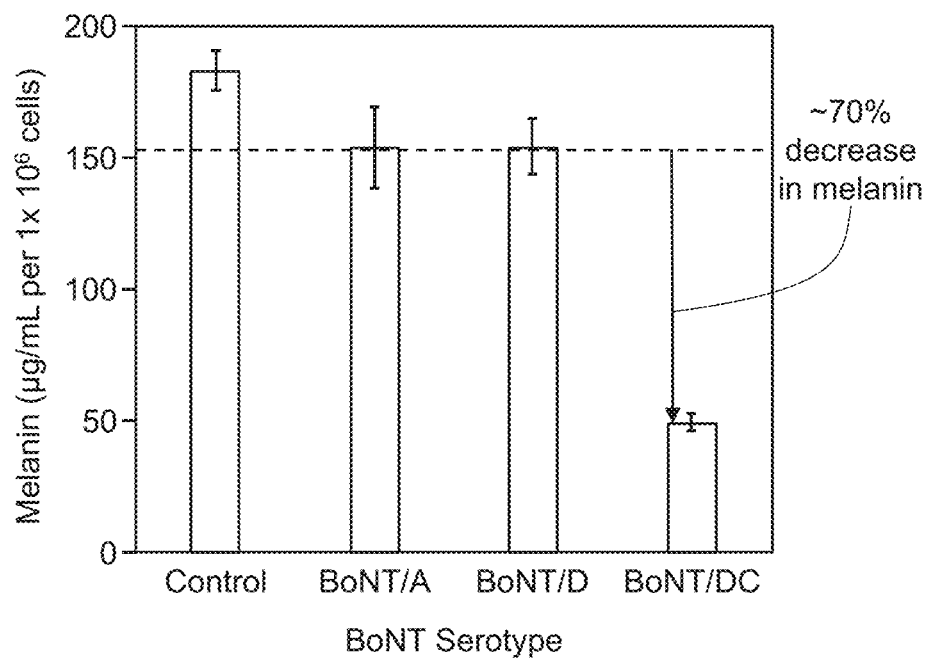
FIG. 2B is a bar graph showing melanin content in mouse melanocyte cells, in μg/mL per $10^6$ cells, after treatment with buffer (untreated or negative control), BoNT/A, BoNT/D, or BoNT/DC.

In studies also detailed in Example 1, mouse melanocyte cells were treated with BoNT/A, BoNT/B, BoNT/C, or BoNT/DC. After a 20 hour treatment, the melanin content was measured and results are shown in FIG. 2A. For the results shown in FIG. 2B, mouse melanocyte cells were treated with either buffer (negative control), BoNT/A, BoNT/D or BoNT/DC. After a 24 hour treatment, melanin content in the cells was measured. The bar graph in FIG. 2B shows melanin level in mouse melanocyte cells, in μg/mL per $10^6$ cells, after treatment with either buffer, BoNT/A, BoNT/D, or BoNT/DC. The data in FIGS. 2A and 2B show that treatment of melanocyte cells with BoNT/DC, but not BoNT/A, BoNT/B, BoNT/C, or BoNT/D, results in decreased melanin levels. Treatment with BoNT/DC achieved at least about 50% decrease in melanin content relative to treatment with another BoNT serotype, such as BoNT/A, BoNT/B, BoNT/C, or BoNT/D, or relative to untreated melanocytes. According, a method of treating a melanin-related affliction is contemplated, where BoNT/DC is administered in an amount that provides at least about 10%, 20%, 30%, 40%, 50%, 60% or 70% decrease in melanin content in melanocytes relative to untreated melanocytes or relative to melanocytes treated with BoNT/A, BoNT/B, BoNT/C, or BoNT/D.

Figure 3:
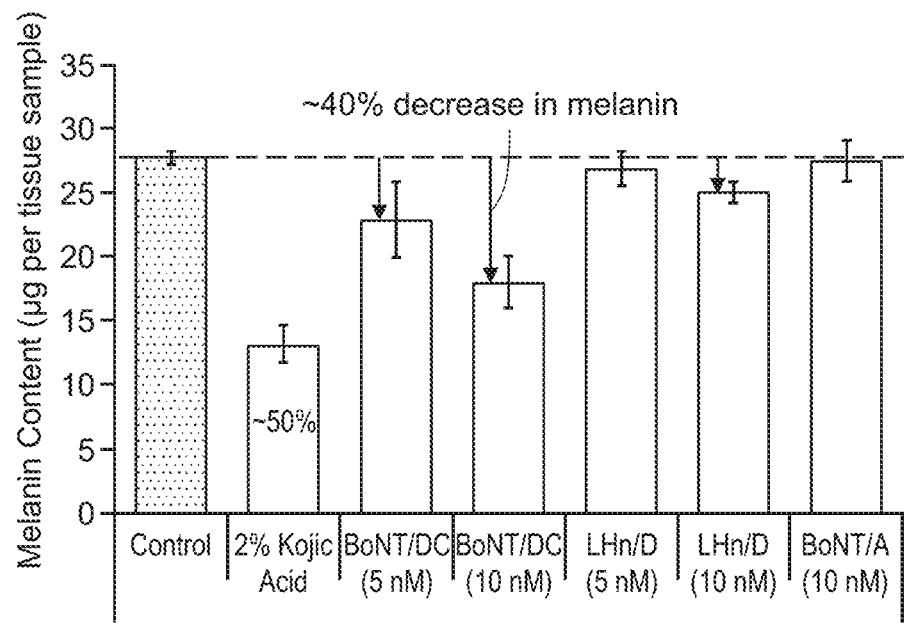
FIG. 3 is a bar graph showing melanin content, in μg per tissue sample, in a human skin equivalent model, after 14 days of either topical treatment with 2% kojic acid (positive control), or treatment with BoNT/DC at 5 nM and 10 nM, LHn/D at 5 nM and 10 nM, or BoNT/A (10 nM)

In another study, as set forth in Example 2, a human skin tissue model based on normal, human-derived epidermal keratinocytes and melanocytes cultured to form a multilayered, highly differentiated model of the human epidermis was obtained. The tissue samples were treated at two concentrations (5 nM or 10 nM) with native BoNT/DC or LHn/D or with 10 nM of native BoNT/A on day 1, 4, 8 and 12 and evaluated for melanin content on day 5, 8, 11 and 15. As controls, some tissue samples were tested in parallel with water (untreated or negative control) or with 2% kojic acid (positive control), applied topically. Representative data where the melanin content in the model tissue measured at day 15 are shown in FIG. 3. Treatment with BoNT/DC, but not with BoNT/A, provided a substantial decrease in melanin levels. The data shows that treatment with 10 nM BoNT/DC achieved about 40% decrease in melanin content compared to treatment at the same concentration with BoNT/A. In this study, viability of the cells in the model tissue after treatment was measured using the MTT assay (MatTek Corp., MTT-100) to confirm that treatment with BoNT/DC did not affect cell viability (data not shown).

Figure 4:
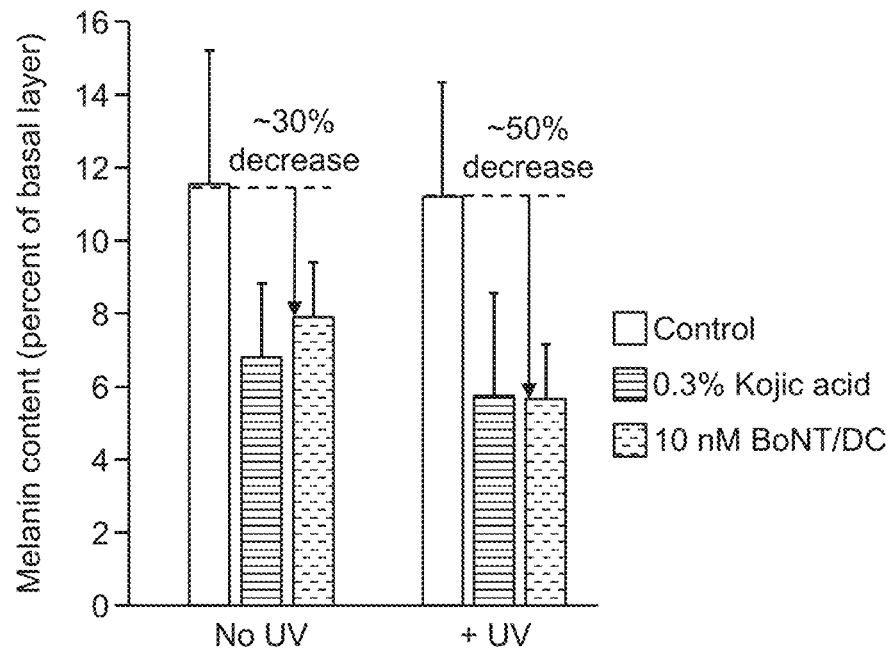
FIG. 4 is a bar graph showing the amount of melanin in the basal layer, measured as percent of basal layer area that stains positive for melanin, based on histology using Masson's Fontana staining, of human skin explants six days after either topical treatment, applied every other day, with 0.3% kojic acid (positive control, bars with horizontal striped fill) or intradermal injection on day 0 with either native BoNT/DC (bars with dashed fill) or buffer (untreated or negative control, open bars), where the samples were not exposed to UV or were exposed to UV.

Another study is described in Example 3. In this study, human skin samples were kept for 10 days with or without daily UV exposure. BoNT/DC was injected intradermally on day 0 and kojic acid was applied topically every other day. The explants were evaluated by histology to assess general morphology (Masson's trichrome) and melanin content (Masson's Fontana) on day 6 of the study. All doses of BoNT/DC (2.5-10 nM) were well tolerated based on histology (data not shown). FIG. 4 shows the melanin content in the tissue explants on day 6 of the study, measured as percent of basal layer area that stained positive for melanin, based on histology using Masson's Fontana staining. Tissue explants treated with native BoNT/DC (bars with dashed fill) and UV exposure had a 50% decrease in melanin content compared to untreated tissue explants (negative control, open bars). Tissue explants treated with native BoNT/DC (bars with dashed fill) and no UV exposure had a 30% decrease in melanin content compared to untreated tissue explants (negative control, open bars). As seen, the whitening effect of 10 nM BoNT/DC is similar to the whitening effect of 0.3% kojic acid (positive control, bars with horizontal striped fill).

Based on these studies, methods for treating disorders and/or diseases associated with melanocyte hyperactivity and/or excess melanin are provided. The methods comprise administering to a patient in need thereof a therapeutically effective amount of a BoNT agent that is (i) taken up by melanocytes and (ii) cleaves, binds to, or sequesters VAMP. In some embodiments, VAMP is VAMP-2. In some embodiments, the agent is a BoNT/DC mosaic toxin.

"BoNT/DC" and "BoNT/DC mosaic" intend a native or recombinant toxin comprising a light chain homologous to the light chain and the translocation domain of BoNT/D and a binding domain homologous to the binding domain of BoNT/C.

Examples of BoNT/DC producing strains include for example BoNT/DC VPI 5995 (ACCESSION: EF378947); BoNT/DC D 4947 (ACCESSION: AB037920); BoNT/DC South Africa (ACCESSION: D38442); BoNT/DC South Africa (ACCESSION: BAA07477); BoNT/DC OFD04, OFD05, OFD08, OFD09, OFD12, OFD13, OFD16, and OFD17 (ACCESSION: AB461914, AB461915, AB461916, AB461917, AB461918, AB461919, AB461920, and AB461921); BoNT/DC It1 (Cedric Woudstra (ANSES, France) (ACCESSION: CM003329 JENO01000000); BoNT/DC DC5 (ACCESSION: NZ_JDRY01000170).

In some embodiments, the toxin mosaic is produced from a non-clostridial source. Examples of non-clostridial toxin mosaic include for example *Weissella oryzae* SG25T.

In some embodiments, the method comprises administering to a patient in need thereof a therapeutically effective amount of BoNT/DC mosaic to cleave VAMP-2 and thereby reduce or decrease melanin content in the cell in order to treat the melanin-related affliction.

Whilst the examples illustrate a preferred BoNT, a skilled artisan will appreciate that the methods may be achieved using other BoNTs, such as other mosaic BoNTs, or a modified neurotoxin which has at least one of its amino acids deleted, modified or replaced, as compared to a native toxin, or the modified botulinum neurotoxin can be a recombinant produced botulinum neurotoxin or a derivative or fragment thereof. In certain embodiments, the modified toxin has an altered cell targeting capability for a neuronal or non-neuronal cell of interest. This altered capability is achieved by replacing the naturally-occurring targeting domain of a botulinum toxin with a targeting domain showing a selective binding activity for a non-botulinum toxin receptor present in a non-botulinum toxin target cell. Such modifications to a targeting domain result in a modified toxin that is able to selectively bind to a non-botulinum toxin receptor (target receptor) present on a non-botulinum toxin target cell (re-targeted). A modified botulinum toxin with a targeting activity for a non-botulinum toxin target cell can bind to a receptor present on the non-botulinum toxin target cell, translocate into the cytoplasm, and exert its proteolytic effect on the target cell. In essence, a botulinum toxin light chain comprising an enzymatic domain is intracellularly delivered to any desired cell by selecting the appropriate targeting domain.

The clostridial toxin, such as a botulinum toxin, for use according to the methods described herein can be stored in lyophilized, vacuum dried form in containers under vacuum pressure or as stable liquids. Prior to lyophilization the botulinum toxin can be combined with pharmaceutically acceptable excipients, stabilizers and/or carriers, such as, for example, albumin, or the like. Acceptable excipients or stabilizers include protein excipients, such as albumin or gelatin, or the like, or non-protein excipients, including poloxamers, saccharides, polyethylene glycol, or the like. In embodiments containing albumin, the albumin can be, for example, human serum albumin or recombinant human albumin, or the like. The lyophilized material can be reconstituted with a suitable liquid such as, for example, saline, water, or the like to create a solution or composition containing the botulinum toxin to be administered to the patient.

In some embodiments, the clostridial derivative is provided in a controlled release system comprising a polymeric matrix encapsulating the clostridial derivative, wherein fractional amount of the clostridial derivative is released from the polymeric matrix over a prolonged period of time in a controlled manner. Controlled release neurotoxin systems have been disclosed for example in U.S. Pat. Nos. 6,585,993; 6,585,993; 6,306,423 and 6,312,708, each of which is hereby incorporated by reference in its entirety.

The amount of a Clostridial toxin selected for local administration to a target tissue can be varied based upon criteria such as the severity of the melanin related affliction being treated, solubility characteristics of the neurotoxin toxin chosen as well as the age, sex, weight and health of the patient. For example, the extent of the area of skin influenced is believed to be proportional to the volume of neurotoxin injected, while the quantity of the melanin related affliction suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14th edition, published by McGraw Hill).

In some embodiments, the therapeutically effective amount is an amount that is sufficient to reduce the melanin content of a patient. In some embodiments, the therapeutically effective amount ranges from about 1 pg (0.001 ng) to about 100 µg. In some embodiments, the therapeutically effective amount ranges from about 0.01 ng to about 10 µg. In some embodiments, the therapeutically effective amount ranges from about 0.1 ng to about 1 µg (1000 ng). In some embodiments, the therapeutically effective amount ranges from about 1 ng to about 500 ng. In some embodiments, the therapeutically effective amount ranges from about 10 ng to about 100 ng. In some embodiments, the therapeutically effective amount ranges from about 0.1 ng to about 10 ng. In some embodiments, the therapeutically effective amount ranges from about 0.01 ng to about 0.1 ng.

In some embodiments, the botulinum toxin mosaic BoNT/DC is administered as a toxin complex comprising the neurotoxic component and non-toxin associated proteins (NAPs). In some embodiments, the BoNT/DC mosaic is administered as a 550 kD complex or a 300 kD complex. In alternative embodiments, BoNT/DC is administered as the neurotoxic component.

The therapeutically effective amount of clostridial toxin, such as botulinum toxin, including a BoNT mosaic, is administered by, for example, injection, such as intramuscular, intracutaneous, intradermal, subcutaneous, or the like, instillation, intravenous, transdermal, and topical. Further for example, the route of administration can be dermal injections, using micro needles or fractional laser.

In some embodiments, the methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a botulinum toxin within a tissue appears to be a function of dose and can be graduated. Jankovic J., et al Therapy With Botulinum Toxin, Marcel Dekker, Inc., (1994), page 150. For example, the neurotoxin can be administered so that the neurotoxin primarily effects dermal cells believed to be involved in the generation of a melanin related affliction.

Local administration of a botulinum toxin, according to the present invention, by injection or topical application to a target tissue provides a superior alternative to systemic administration of pharmaceuticals to patients to alleviate a melanin related affliction.

The disorders and/or diseases associated with melanocyte hyperactivity and/or excess melanin include, for example, hyper melanogenesis, hyperpigmentation associated with melasma, solar lentigines (age-spots), nevi on the skin, and melanoma.

In some embodiments, a method of cleaving VAMP is provided. The method comprises contacting a toxin with VAMP. In some embodiments, the toxin is a clostridial toxin, such as a botulinum toxin, fragments or variants thereof. In some embodiments, the toxin is a botulinum toxin mosaic, fragments or variants thereof. In alternative embodiments, the toxin is a non clostridial toxin mosaic, fragments or variants thereof. In some embodiments, the botulinum toxin is BoNT/D, fragments or variants thereof. In some embodiments, the method comprises contacting BoNT/D light chain (LC/D) with VAMP. In other embodiments, the botulinum toxin is BoNT/DC. In some embodiments, VAMP is VAMP-2 or VAMP-3. In some embodiments, the method comprises contacting BoNT/DC or BoNT/D light chain (LC/D), with VAMP-2 or VAMP-3.

In some embodiments, a method of cleaving VAMP-2 is provided. The method comprises contacting a botulinum toxin, fragments or variants thereof with VAMP-2. In some embodiments, the botulinum toxin, fragments or variants thereof is provided in an amount that achieves at least 10%, at least 20%, at least 30%, at least 50%, at least 70%, at least 80%, at least 90% or substantially complete (e.g., 100%) cleavage of VAMP-2. In some embodiments, the botulinum toxin, fragments or variants thereof comprises BoNT/D, BoNT/D light chain (LC/D), BoNT/B, or BoNT/B light chain (LCB). In these embodiments, VAMP may be either recombinant VAMP or from lysed melanocytes or from melanocytes in vivo.

In some embodiments, a method of cleaving VAMP-2 and reducing melanin content in melanocytes is provided. The method comprises contacting melanocytes with a botulinum toxin, fragments or variants thereof. In some embodiments, the botulinum toxin is BoNT/DC mosaic. In some embodiments, the BoNT/DC mosaic is provided in an amount that achieves at least 10%, at least 20%, at least 30%, at least 50%, at least 70%, at least 80%, at least 90% or substantially complete (e.g., 100%) cleavage of VAMP-2 in melanocyte cells.

III. Examples

Without intending to limit the scope of the disclosure, example embodiments are set forth by the following Examples.

Example 1

Treatment of Melanocytes with BoNT/DC Reduces Melanin Content

Normal mouse melanocyte (Melan-a) cells were grown in growth medium in 6-well plates until ~80% confluence. The cells were treated in duplicate with 10 nM of either buffer (untreated or negative control), native BoNT/A, native BoNT/B, recombinant BoNT/D, native BoNT/DC or recombinant LHn/D in serum free medium. The cells were treated for 24 hours with the toxins and then incubated in serum free media for 96 hours.

After incubation for 96 hours, VAMP-2 and GADPH were detected by Western Blot using anti-VAMP-2 and anti-GAPDH. The melanin content was measured using SOLVABLE™ (PerkinElmer) melanin assay. Results are shown in FIGS. 1A-1B.

In a similar study, normal mouse melanocyte (Melan-a) cells were grown in growth medium in 6-well plates until ~65-75% confluence and treated in triplicate 10 nM of either native BoNT/A, BoNT/B, BoNT/C, or BoNT/DC in serum free medium for 20 hours, followed by incubation in serum free media for another 96 hours. The melanin content was measured using SOLVABLE™ (PerkinElmer) melanin assay. Results are shown in FIG. 2A.

In a similar study, normal mouse melanocyte (Melan-a) cells were grown in growth medium in 6-well plates until ~80% confluence and treated in triplicate with buffer (untreated or negative control), 10 nM of native BoNT/A, recombinant BoNT/D, or native BoNT/DC in serum free medium for 24 hours, followed by incubation in serum free media for another 96 hours. The melanin content was measured using SOLVABLE™ (PerkinElmer) melanin assay. Results are shown in FIG. 2B.

Example 2

BoNT/DC Reduces Melanin Content in Human Skin Equivalent Model

A human skin tissue model, MELANODERM™ (MatTek Corporation) was obtained. This model is based on normal, human-derived epidermal keratinocytes and melanocytes cultured to form a multilayered, highly differentiated model of the human epidermis. The tissues are three dimensional co-cultures with the melanocytes and keratinocytes in a 1:10 ratio. The tissue samples were treated in duplicate with buffer (untreated control), 5 nM or 10 nM of either native BoNT/DC, native BoNT/A, or LHN/D as a negative control for unspecific uptake, by basal delivery in the media on day 1, 4, 8 and 12 and evaluated for melanin content on day 5, 8, 11 and 15. As controls, some tissue samples were tested in parallel with water (untreated control) or with 2% kojic acid (positive control), applied topically.

The tissue samples were treated on day 1, 4, 8 and 12 and evaluated for melanin content on day 5, 8, 11 and 15 using SOLVABLE™ (PerkinElmer) melanin assay. Cell viability was assessed using MTT assay (MatTek Corp., MTT-100). Treatment with BoNT/DC did not affect cell viability based on MTT assay (data not shown). Melanin contents evaluated on day 15 are shown in FIG. 3.

Example 3

BoNT/DC Reduces Melanin Content in Human Explant Skin

Human skin explants from abdominoplasty from a 45-year Caucasian female were kept for 10 days with or without daily UV exposure (Day 0-8). BoNT/DC was injected intradermally (50 µL) on day 0 and kojic acid was applied topically every other day. The explants were evaluated by histology to assess general morphology (Masson's trichrome) and melanin content (Masson's Fontana) on day 6 of the study.

All doses of BoNT/DC (2.5-10 nM) were well tolerated based on histology (data not shown). The percentage of melanin in the tissue explants is shown in FIG. 4, where bars correspond to the treatment as follows: tissue explants six days after intradermal injection with native BoNT/DC (bars with dashed fill), with topically applied kojic acid as a positive control (bars with horizontal striped fill) and untreated (control, open bars). The whitening effect of 10 nM BoNT/DC is similar to the whitening effect of 0.3% kojic acid.

Example 4

Treatment of Solar Lengitines by BoNT/DC

A 45 year female with phototype II skin shows hyperpigmented uneven brown discoloration, dark spots of varying size, on her face, which are diagnosed as solar lentigines. She receives intraepidermal treatment with a formulation of BoNT/DC toxin. A topical anesthetic cream is applied on the skin 30 min and completely removed before treatment.

1.5 µg vacuum-dried powder of BoNT/DC toxin is dissolved in 1 mL of sterile 0.9% saline to constitute a 10 nM solution which is injected into the upper dermis of her facial skin spots using a 30-G needle. The toxin is injected at 50 µL per injection site with injections about every 1 $cm^2$ apart. The injection depth is about 0.5 mm. A total of about 1.5 µg is injected into the patient's face.

Evaluation is conducted at baseline and at 3 weeks post-treatment. Quantitative assessment of pigmentation is done using Canfield RBX imaging technology. Compared to baseline, at 3 week post-treatment, her facial skin shows significant lighting of spots based on imaging; and she scores higher physician's global assessment and subject satisfaction score, from severe to mild overall pigmentation.

Example 5

Treatment of Melasma by BoNT/DC

A 37 year pregnant female with phototype III skin presents with hyperpigmented discoloration, brown irregular spotty patches on her cheeks, nose, upper lip, and forehead, which are diagnosed as Melasma. She receives intraepidermal treatment with a formulation of BoNT/DC toxin.

4.5 µg vacuum-dried powder of BoNT/DC toxin is dissolved in 3 mL of sterile 0.9% saline to constitute a 10 nM solution which is injected into the epidermis of her facial skin using a multineedle dermal injector system. The areas which show discolorations is injected with the toxin solution at multiple injection sites, the injection sites are about 2 mm apart, at 2 µL per injection point. The injection depth is about 0.1 mm. A total of about 4.5 µg is injected into the patient face.

Evaluation is conducted at baseline and at 3 weeks post-treatment. Quantitative assessment of pigmentation is done using Canfield RBX imaging technology. Compared to baseline, at 3 weeks post-treatment, her facial skin shows significant less discoloration; and she scores higher physician's global assessment and subject satisfaction score, from severe to mild overall pigmentation.

While several exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method of treating a disorder or affliction associated with melanocyte hyperactivity or excess melanin production in a patient in need thereof, comprising administering to the patient a therapeutically effective amount of BoNT/DC, thereby treating the disorder or affliction associated with melanocyte hyperactivity or excess melanin production in the patient.

2. The method of claim 1, wherein the disorder or affliction is selected from the group consisting of hyper melanogenesis, hyperpigmentation, melasma, solar lentigos, nevi, and melanoma.

3. The method of claim 1, wherein said administering comprises administering a liquid composition comprising BoNT/DC.

4. The method of claim 3, wherein the liquid composition comprises one or more of a tonicity agent and a surfactant.

5. The method of claim 1, wherein said administering is via dermal injection.

6. The method of claim 1, wherein said administering comprises administering a solid composition comprising BoNT/DC.

7. The method of claim 1, wherein said administering is topically administering.

8. A method for treating a hypermelanin-related affliction of the skin in a patient in need thereof, comprising: administering to the skin of the patient a composition comprising BoNT/DC, thereby treating the hypermelanin-related affliction of the skin in the patient.

9. The method of claim 8, wherein the affliction is selected from the group consisting of hyper melanogenesis, hyperpigmentation, melasma, solar lentigos, nevi, and melanoma.

10. The method of claim 8, wherein said administering comprises administering a liquid composition comprising BoNT/DC.

11. The method of claim 10, wherein the liquid composition comprises one or more of a tonicity agent and a surfactant.

12. The method of claim 8, wherein said administering is via dermal injection.

13. The method of claim 8, wherein said administering comprises administering a solid composition comprising BoNT/DC.

14. The method of claim 8, wherein said administering is topically administering.

15. A method for treating hyperpigmentation of the skin in a patient in need thereof, comprising administering to the skin of the patient a composition comprising BoNT/DC; thereby treating hyperpigmentation of the skin in the patient.

16. The method of claim 15, wherein said administering comprises administering a liquid composition comprising BoNT/DC.

17. The method of claim 16, wherein the liquid composition comprises one or more of a tonicity agent and a surfactant.

18. The method of claim 15, wherein said administering is via dermal injection.

19. The method of claim 15, wherein said administering comprises administering a solid composition comprising BoNT/DC.

20. The method of claim 15, wherein said administering is topically administering.

* * * * *